(12) United States Patent
Montagu

(10) Patent No.: US 6,643,076 B2
(45) Date of Patent: Nov. 4, 2003

(54) ATTACHMENT DEVICE

(75) Inventor: Jean I. Montagu, Brookline, MA (US)

(73) Assignee: Affymetrix, Inc., Santa Clara, CA (US)

( * ) Notice: Subject to any disclaimer, the term of this patent is extended or adjusted under 35 U.S.C. 154(b) by 107 days.

(21) Appl. No.: 09/870,558

(22) Filed: May 31, 2001

(65) Prior Publication Data

US 2002/0018202 A1 Feb. 14, 2002

Related U.S. Application Data

(60) Provisional application No. 60/208,885, filed on Jun. 2, 2000.

(51) Int. Cl.$^7$ .............................. G02B 7/02; G11B 17/30
(52) U.S. Cl. ...................... 359/819; 359/811; 359/822; 369/219
(58) Field of Search .................. 359/819, 811, 359/820, 822, 827; 369/219, 44.15

(56) References Cited

U.S. PATENT DOCUMENTS

| | | | |
|---|---|---|---|
| 3,994,050 A | 11/1976 | Bub ............................ 24/255 |
| 4,103,860 A | 8/1978 | Haas et al. ................. 248/467 |
| 4,397,438 A | 8/1983 | Chapman .................... 248/229 |
| 4,662,717 A | 5/1987 | Yamada et al. ............. 359/362 |
| 4,850,674 A | 7/1989 | Hasselskog ................. 359/820 |
| 4,869,582 A | 9/1989 | Nakajima et al. ........... 359/871 |
| 4,941,740 A | 7/1990 | Sigman ...................... 359/224 |
| 4,973,145 A | 11/1990 | Kirkwood et al. .......... 359/872 |
| 4,984,882 A | 1/1991 | Boyd ......................... 359/871 |
| 5,373,496 A | * 12/1994 | Tomita et al. .............. 369/219 |
| 5,446,822 A | 8/1995 | Keith .......................... 385/135 |
| 5,550,669 A | 8/1996 | Patel ........................... 359/224 |
| 5,592,337 A | 1/1997 | Hama ......................... 359/872 |
| 5,642,235 A | 6/1997 | Ichikawa .................... 359/811 |
| 5,754,350 A | 5/1998 | Sato ........................... 359/818 |
| 5,801,891 A | 9/1998 | Lloyd ......................... 359/871 |
| 6,098,947 A | 8/2000 | Kerschner ................... 248/466 |
| 6,130,788 A | 10/2000 | Nomura et al. ............. 359/694 |
| 6,157,501 A | 12/2000 | Sato et al. .................. 359/819 |
| 6,392,825 B1 | * 5/2002 | Trunz et al. ................ 359/819 |

OTHER PUBLICATIONS

Paul R. Yoder, Jr., Opto–Mechanical System Design, Second Edition, Revised and Expanded, 659 pages, 4th Printing, Publisher: Marcel Dekker, New York, NY –Book Enclosed.
Paul R. Yoder, Jr., Mounting Lenses in Optical Instruments, vol. TT 21, 179 pages, Publisher: SPIE Optical Engineering Press, Bellingham, Washington –Book Enclosed.

* cited by examiner

*Primary Examiner*—Jordan M. Schwartz
*Assistant Examiner*—Tim Thompson
(74) *Attorney, Agent, or Firm*—Alan Sherr; Leticia Block; Philip McGarrigle

(57) ABSTRACT

An attachment device is described for attaching a part to a structure. The part may be, for example, an optical element such as a lens or a mirror, that is to be attached, for example, to an optical instrument such as a scanner used to scan biological materials. The device includes a base and two or more holding elements coupled to the base. The holding elements may include a first group of two or more opposing holding elements of a first length and a second group of two or more opposing holding elements of a second length shorter than the first length. Each holding element flexibly engages at least one surface of the part when the device is engaged with the part. A third group of two or more opposing holding elements may also be provided that also are shorter than the first length and that rigidly engage the part. The base and the holding elements may be formed of a single piece of flexible material.

14 Claims, 4 Drawing Sheets

ATTACHMENT DEVICE

RELATED APPLICATION

This application is related to and claims priority from U.S. Provisional Patent Application No. 60/208,885, titled "Attachment Device," filed on Jun. 2, 2000, which is hereby incorporated herein by reference for all purposes.

FIELD OF THE INVENTION

The present invention relates to the field of attachment devices and, more particularly, to attachment devices for use in optical systems.

BACKGROUND

One field in which optical systems play an important role involves the capture of fluorescent signals indicating hybridization of labeled target biological samples with probes on synthesized or spotted probe arrays. Synthesized nucleic acid probe arrays, such as Affymetrix® GeneChip® probe arrays from Affymetrix, Inc. of Santa Clara, Calif., have been used to generate unprecedented amounts of information about biological systems. For example, a commercially available GeneChip® array set is capable of monitoring the expression levels of approximately 6,500 murine genes and expressed sequence tags (EST's). Experimenters can quickly design follow-on experiments with respect to genes, EST's, or other biological materials of interest by, for example, producing in their own laboratories microscope slides containing dense spotted arrays of probes using the Affymetrix® 417™ Arrayer or other spotting devices. Analysis of data from experiments with synthesized and/or spotted arrays may lead to the development of new drugs and new diagnostic tools.

The optical devices used to capture these fluorescent signals from labeled biological samples often are referred to as scanners. Due to the relatively small emission signals sometimes available from the hybridized target-probe pairs, the presence of background fluorescent signals, the high density of the arrays, variations in the responsiveness of various fluorescent labels, and other factors, care must be taken in designing scanners to properly acquire and process the fluorescent signals indicating hybridization. For example, U.S. Pat. No. 6,171,793 to Phillips, et al., hereby incorporated herein in its entirety for all purposes, describes a method for scanning probe arrays to provide data having a dynamic range that exceeds that of the scanner.

Scanners, like other optical systems, generally incorporate a number of mirrors, lenses, and more specialized optical elements that typically are attached to a structure. Various types of conventional devices have been designed to secure these elements to the structure to provide reliable attachment. Conventional attachment devices are described, for example, in P. Yoder, *Opto-Mechanical Systems Design* (2d ed., Marcel Dekker 1993), and in P. Yoder, *Mounting Lenses in Optical Instruments* (SPIE Optical Engineering Press 1995), both of which are hereby incorporated herein by reference in their entireties. Nonetheless, there is a continuing need to improve scanner design, and the design of other kinds of optical instruments, to provide more accurate and reliable signals and thus provide experimenters with more sensitive and accurate data.

SUMMARY OF THE INVENTION

The optical elements of a scanner may be subject to various forces due to movement of the instrument. There thus is a need for securing those elements without deforming or distorting them or otherwise interfering with their characteristics and operation. Scanners and scanner attachment devices that address these and other needs are described herein with respect to illustrative, non-limiting, implementations.

In some embodiments, not necessarily limited to scanners or optical instruments, an attachment device is described for attaching a part to a structure. The device includes a base and two or more holding elements coupled to the base. The holding elements include a first holding element of a first length and a second holding element of a second length. In some implementations, the second length may be shorter than the first length. Each holding element flexibly engages at least one surface of the part when the device is engaged with the part. The part may, but need not, be an optical element, for example, a mirror, a lens, or a mirror or lens assembly. The base and the holding elements may be formed of a single piece of flexible material.

In some implementations of these embodiments, the attachment device also includes opposing holding elements that are constructed and arranged to rigidly engage opposing side surfaces of the part. Those opposing holding elements may be constructed and arranged, together with the base, to form a substantially flat surface both when the device is engaged with the part and when the device is not engaged with the part. Those opposing holding elements rigidly engage the part, even though they may be made of the same piece of flexible material as are the base and the holding elements that flexibly engage the part. This is so because, in these non-limiting implementations, they lie substantially flat, i.e., are substantially parallel to the base, and are subject to buckling rather than bending or flexing. Thus, the rigidly engaged holding elements resist compression when forces substantially parallel to the base are applied to them. In contrast, the flexibly engaged holding elements form an angle with the flat surface of the base to which they are coupled, and thus flex when a force substantially parallel to the base is applied to them. In various of these implementations, the base has at least two securing elements that secure the device to the structure, each of which may be aligned in proximity to one of the opposing holding elements.

In some implementations, the device is formed from a single piece of flexible material having a substantially flat surface. When disengaged from the part, the device may revert to the substantially flat surface, i.e., it may return to a substantially flat shape. The word "substantially" means in the contexts of this and the preceding paragraphs that the device, in the shape from which it is made from the flexible material and the shape it assumes after disengagement from the part, is generally flat but not necessarily perfectly flat. For example, the flexible material from which the device is made may have bumps, waves, burrs, and other irregularities or imperfections such as may be expected, for instance, in typical commercial molding or stamping operations. The device may also be made from flexible material that is not substantially flat, but the device may thereafter be substantially flattened. Also, when the device is disengaged from the part, some portions of the device, such as the holding elements that flexibly engage the part, may not completely return to their original substantially flat state. That is, they may protrude somewhat from the plane of the support regions or of other holding elements due to the less than perfect elasticity of the flexible material. These protrusions may increase in proportion to the number of times the device is engaged and disengaged from a part. However, any such deviations from flatness, either in the original shape of the device or the shape it takes after being disengaged from a part, are incidental and are not related to the functioning of the device.

In various implementations, two or more opposing holding elements exert forces on at least one surface of the part. These forces are due, at least partially, to deformation of the opposing holding elements from the substantially flat surface when the device is engaged with the part. Also, these forces may be due, at least partially, to deformation of a portion of the base from the substantially flat surface when the device is engaged with the part. Each of the forces may include components perpendicular and/or parallel to the substantially flat surface. As used in this context, the word "opposing" is used broadly to mean that the holding elements may, when engaged with the part, exert partly or wholly opposing forces on the part so as to resist movement. It is therefore not necessary in all implementations that the holding elements be exactly opposite from each other, such as pairs of sides of a square, or even that they be regularly opposed around the part, such as the three sides of an equilateral triangle surrounding the part.

The first and second holding elements may be adjacent or near to each other. In these cases, when the device is engaged with the part, the second holding element may be deformed from the substantially flat surface due, at least in part, to the first holding element being deformed from the substantially flat surface.

In various implementations, the base has at least one securing element that secures the device to the structure. The securing element may be, for example, an aperture for accepting a coupling element, such as a screw or bolt. Alternatively, the securing element may be a bonding element, such as a weld or glue.

With respect to some specific embodiments, a scanner is described that includes an optical element, a support structure, and a device that attaches the optical element to the support structure. The attachment device includes a base having at least one securing element that secures the device to the support structure. The device also includes a plurality of holding elements coupled to the base including a first holding element of a first length and a second holding element of a second length shorter than the first length. Each holding element flexibly engages at least one surface of the optical element when the device is engaged with the optical element.

Also described herein is a device for holding an optical element in a semi-rigid manner. The term "semi-rigid" used in this context means that the optical element is restrained from moving to an extent that typically would adversely affect its optical characteristics or operations. However, the optical element need not have been rendered absolutely immovable, as if it had been welded or bolted to a support structure. The device also includes a base and a plurality of deformable elements coupled to the base so as to surround the optical element and retain it by applying axial and lateral forces. The degree of "semi-rigidity" with which the optical element is held is related to the flexibility of the deformable elements. The base and the deformable elements are formed from a single piece of material.

Yet a further embodiment is a scanner that includes a support structure, an optical element, and a device for attaching the optical element to the structure in a semi-rigid manner. The device includes a base and a plurality of deformable elements coupled to the base so as to surround the optical element and retain it by applying axial and lateral forces. The base and deformable elements are formed from a single piece of material.

In an additional embodiment, a system is described for detecting one or more biological materials. The system includes a probe array having a plurality of tags capable of fluorescing. The tags are coupled to the biological materials. Also included in the system is a scanner that has a support structure, an optical element, and a device for attaching the optical element to the support structure in a semi-rigid manner. The attachment device includes a base and a plurality of deformable elements coupled to the base so as to wholly or partially surround the optical element and retain it by applying axial and lateral forces. The base and deformable elements are formed from a single piece of material. The system further includes a radiation source that generates an excitation beam that passes through the optical element and excites the plurality of tags, causing them to fluoresce. In some implementations of this embodiment, fluorescent emissions from the plurality of tags also pass through the optical element. The probe array may be, as non-limiting examples, a spotted probe array or a synthesized probe array.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments or implementations. Also, any one or more function, step, operation, or technique described elsewhere in this specification may, in alternative embodiments or implementations, be combined with any one or more function, step, operation, or technique described in the summary. Thus, the above embodiments and implementations are illustrative rather than limiting.

DETAILED DESCRIPTION

Figure 1:
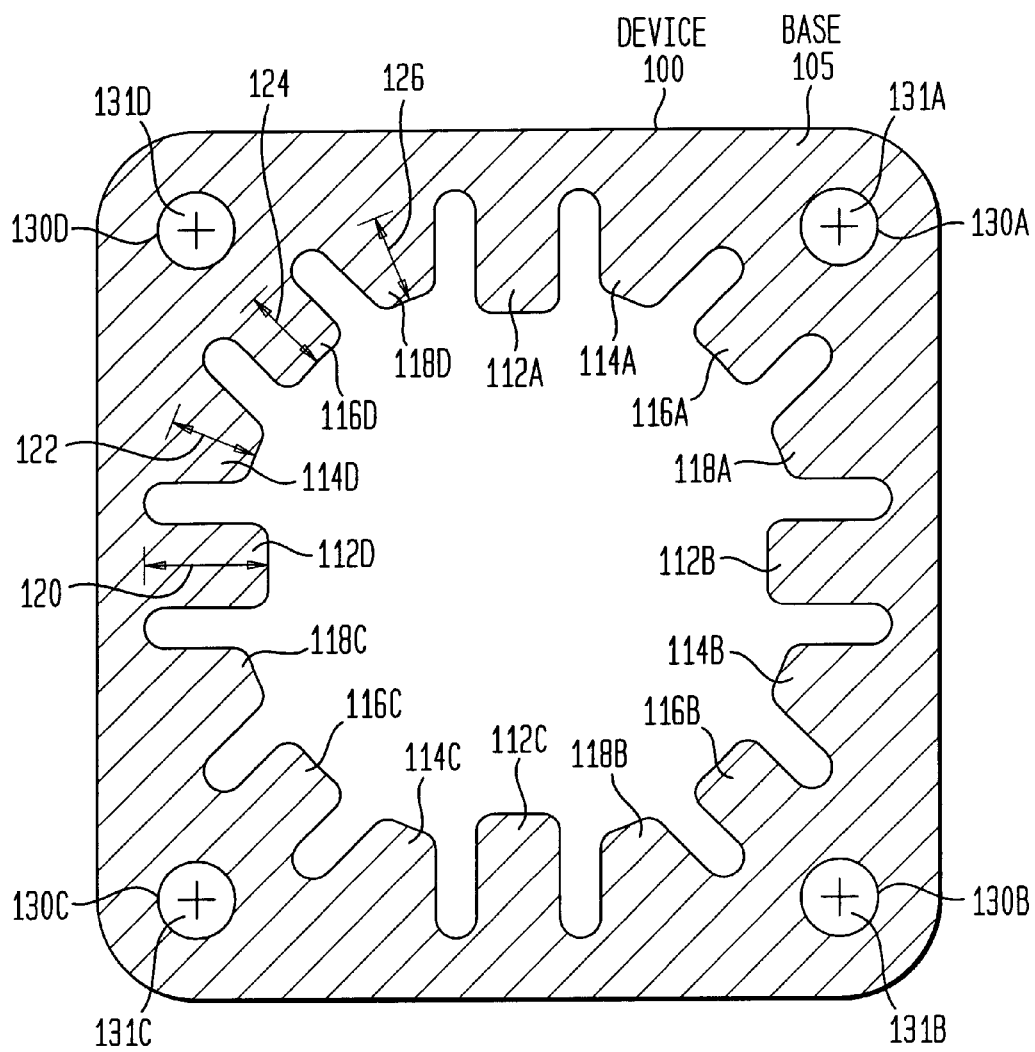
FIG. 1 is an overhead plan view of one embodiment of a device for attaching an optical element to a structure.
Figure 2A:
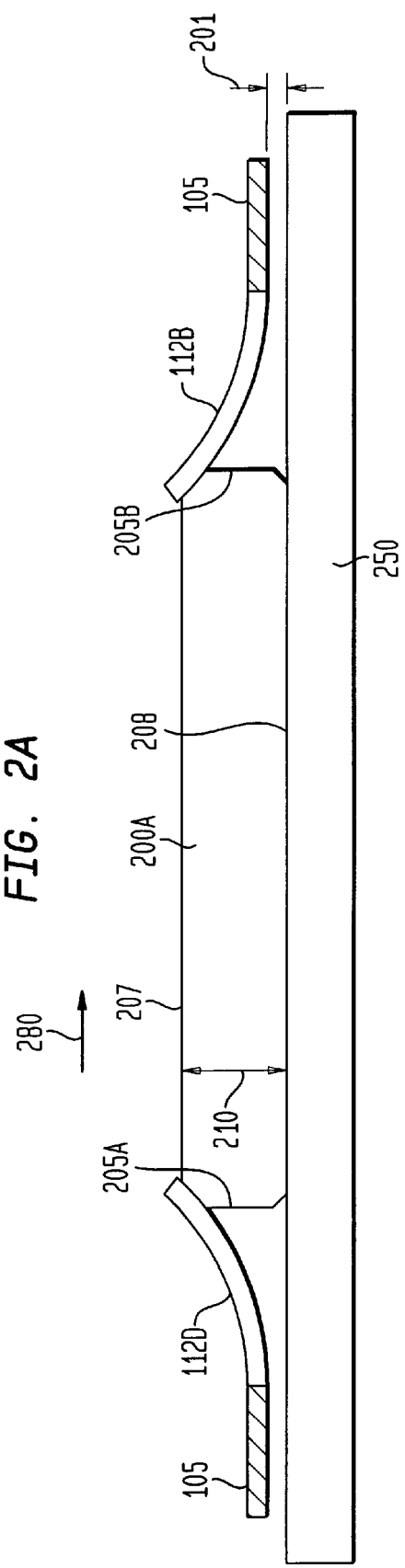
FIGS. 2A, 2B, and 2C are cross-sectional side views of the device of FIG. 1 secured to a support structure and respectively showing illustrative implementations of first, second, and third pairs of opposing holding members engaging an optical element.
Figure 2B:
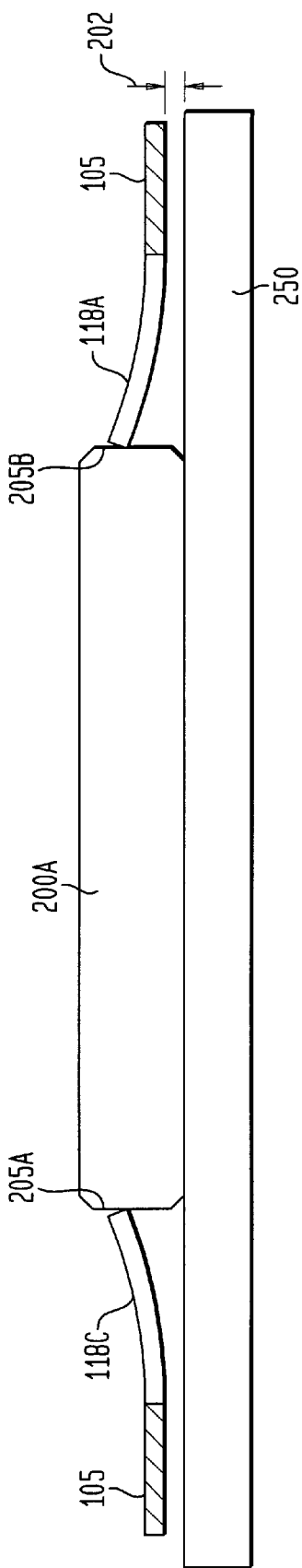
Figure 2C:
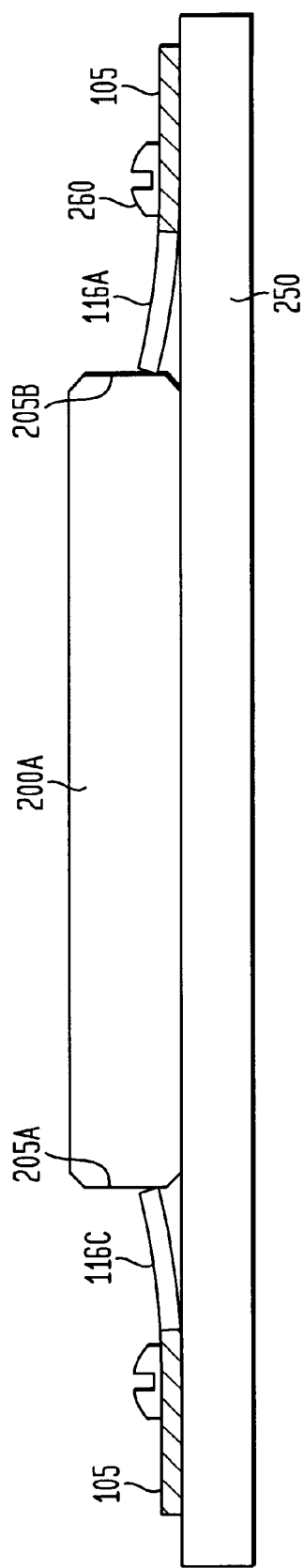
Figure 3:
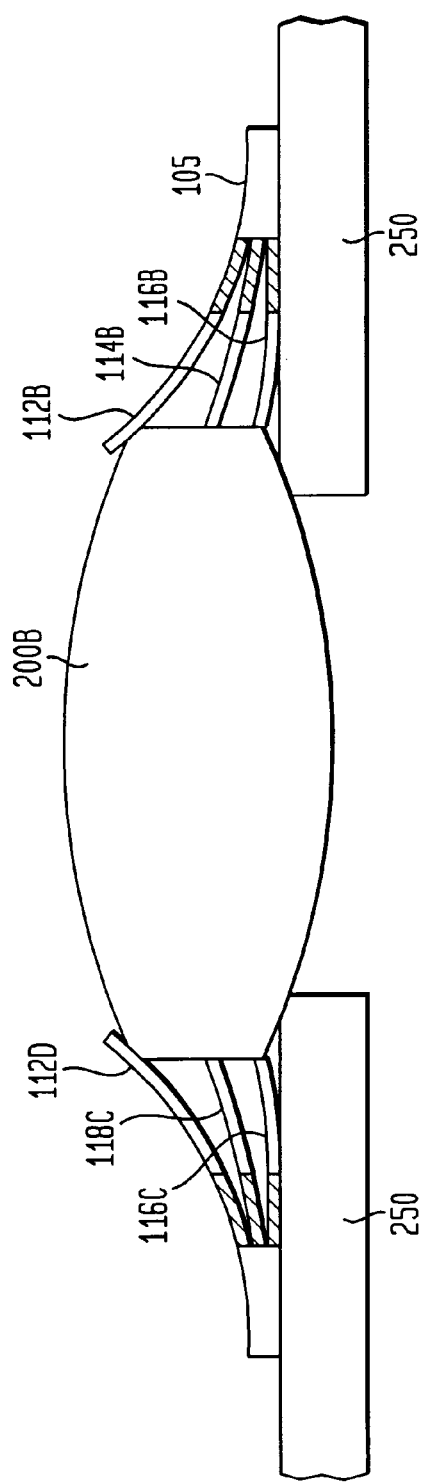
FIG. 3 is a side view of the device of FIG. 1 secured to a support structure and showing illustrative implementations of first, second, and third opposing pairs of holding members flexibly and cooperatively engaging an optical element.

An attachment device for securing a part, such as an optical element, to a support structure is now described in relation to the illustrative implementations shown in FIGS. 1–3. Various alternatives, modifications and equivalents are possible. For example, certain specific attachment devices and instruments are described herein using exemplary implementations for analyzing data from spotted arrays produced by the Affymetrix® 417™, 427™, or 437™ Arrayers (available from Affymetrix, Inc. of Santa Clara, Calif.). The attachment devices may be used, for example, to attach optical elements to support structure of the Affymetrix® 428™ Scanner (available from Affymetrix). However, these attachment devices also may be applied with respect to many other types of scanners and other optical instruments, and may further be used for attaching parts in instruments other than optical ones. Moreover, scanners employing attachment devices described herein are not limited to use with spotted probe arrays made using spotters from Affymetrix or others, nor are they limited for use with Affymetrix® GeneChip® arrays or other synthesized arrays. Rather, these scanners may be used with respect to numerous parallel biological assays produced in accordance with a variety of conventional technologies and/or produced in accordance with techniques that may be developed in the future. For example, the systems, methods, and products described herein may be applied to scanning parallel assays of nucleic acids, PCR products generated from cDNA clones, proteins, antibodies, or many other biological materials. These materials may be disposed on slides (as typically used for spotted arrays), on substrates employed for GeneChip® arrays, or on beads, optical fibers, or other substrates or media. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

FIG. 1 is an overhead plan view of illustrative attachment device 100. Device 100 holds a part, such as an optical element (not shown in FIG. 1), with minimal and predictable stresses and without the use of bonding agents. Moreover, device 100 may quickly and easily be engaged with a part. Device 100 is designed to restrain the part (hereafter referred to simply as an illustrative "optical element") against linear acceleration forces and torques in all three linear and all three angular degrees of freedom. These forces may occur, for example, if the instrument is dropped or moved quickly. Device 100 similarly is designed to restrain the optical element against angular accelerations. Types of optical elements for which device 100 may be employed include mirrors (e.g., dichroic mirrors), lenses made of all types of glasses (e.g., fused silica, borosilicate glass, sodalime glass, and other conventional glasses), as well as many other types of optical elements (or other kinds of parts) now in use or that may be developed in the future.

Advantageously, device 100 holds an optical element so that it is immobilized and may be attached to a structure with minimal deformation or stressing, and without appreciably impinging on optically active areas of the optical element. Lack of deformation and stressing are desirable characteristics because stresses may alter the element's optical properties or its flatness, curvature, or other aspect of shape that affect its performance. Stresses may also occasionally induce birefringence or affect other =properties of the index of refraction. Also, radial movement of the optical element, i.e., movement so that the alignment of the element with the optical axis is affected, may dramatically degrade the ability of the element to perform as expected. For example, a dichroic mirror often is not evenly coated over its surface so that, if the mirror is translated laterally with respect to the optical axis, the reflectivity of the portion of the mirror upon which a light beam impinges may not be as expected. If the optical element is a lens, a radial shift could have even more dramatic and undesirable consequences for focusing the beam, as will be evident to those of ordinary skill in the relevant art. Another example is a pin-hole element that may be used to provide a desired depth of field. If the pin-hole element shifts with respect to the optical axis, the effective size of the hole may be reduced, or the light beam may be blocked completely.

In certain types of optical instruments it is especially important that deformation of optical elements be avoided. For example, scanners used to analyze biological probe arrays may be used to detect faint fluorescent light from features on a scale of 100, 50, or 10 microns, or less. Accordingly, it is important that lenses and mirrors in these scanners be attached without deformation in order both to retain the integrity of the laser illumination going to the probe array substrate and the integrity of the emission of light returned from a fluorescent molecule. Scanners that exemplify this use are shown in PCT/US99/06097; U.S. Pat. Nos. 5,143,854; 5,578,832; 5,631,734; 5,834,758; 5,856, 101; 5,936,324; 5,981,956; 6,025,601; U.S. patent application Ser. Nos. 09/500,548, now U.S. Pat. No. 6,407,858, and 09/079,790 now U.S. Pat. No. 6,262,838; and U.S. Provisional Patent Application Ser. No. 60/286,578, all of which are hereby incorporated by reference in their entireties for all purposes. Examples of substrates that are scanned include microarrays that are created by direct placement of reagents on the surface of the substrate. Reagents include polymers, ligands and receptors as described in U.S. Pat. Nos. 5,744, 305, 5,445,934, 6,040,193, 5,677,195, 5,631,734, 5,624,711, 5,599,695, 5,510,270, 5,451,683, 5,424,186, 5,412,087, 5,405,783, 5,384,261, 5,252,743 and 5,143,854, all of which patents are hereby incorporated by reference in their entireties for all purposes. The above devices are used in analyzing nucleic acid sequences as shown in the above patents and in U.S. Pat. No. 6,040,138, also hereby incorporated by reference.

The anchoring of optic elements, commonly made of glass, is complicated by the fact that their coefficient of thermal expansion is often only a fraction of that of the structural elements of the instrument's frame where they are installed. It is common to mount the glass within a metal support with equal thermal expansion characteristics, typically a NiFe alloy. The mounts then fastened to the structure. However, because the thermal expansion characteristics of the metal support and the structural elements differ, deformations and shifting may occur. Even if this is not the case, the metal support adds weight and complexity to the instrument.

Alternatively, the optical element may be mounted onto an aluminum or brass support with an epoxy that yields when stressed. However, deformation may occur when epoxy is used because the epoxy often will dry unevenly. In order to minimize the deformation induced by the epoxy during the attachment process, much larger optical elements often are used so that they will resist deformation or at least to provide that the region of interest is not deformed. The use of epoxy is delicate, however, and necessitates protection of the operator. Thus, epoxy frequently is applied in an isolated environment, thereby increasing the complexity and cost of production. Moreover, great care must be given to the prevention of undesirable leakage of epoxy, which may cause deformation as it solidifies and shrinks unpredictably.

Additionally, it generally is desirable that the optical element be attached without significantly obscuring optically active areas of its surfaces. That is, the attachment device advantageously should be designed so as not to have elements that fit over significant portions of the optical surfaces of the optical element. Device 100, and numerous other implementations of the present invention, hold the optical element with little or no impingement on optically active areas, as is explained in greater detail below with respect to the operations of holding elements 112, 114, 116, and 118 of the illustrated example.

Device 100 includes a base portion 105. One or more securing elements 130 are provided to secure base 105 to a support structure of an instrument (not shown in FIG. 1). For example, holes 130A, B, C, and D, generally and collectively referred to hereafter as holes 130, are provided in the illustrated implementation so that screws 131 may be used to secure base 105 to the structure. As is evident, bolts, rivets, staples, snap-in clips, or a wide variety of similar members could alternatively be used. Also, rather than being secured using holes 130, the securing elements in alternative implementations may consist of welds, glues, or other bonding materials or methods. As described in greater detail below, device 100 also includes a plurality of holding members 112, 114, and 118 designed to flexibly engage the optical element, and further includes in this implementation a plurality of holding members 116 designed to rigidly engage the optical element.

Device 100 typically is manufactured to accommodate the particular optical element or other part that it will retain. That is, device 100 in a particular implementation typically is designed to hold down, for example, an optical element of specified geometry and dimension. For example, device 100 of the illustrated implementation is designed to engage a circular optical element. As noted, some of the holding elements of device 100 flex when device 100 is engaged with the optical element, and this flexure typically occurs along the holding element, particularly near where they merge into base 105, and in areas of base 105 near the flexing holding elements. Flexure occurs in this manner due to the shapes and dimensions of the holding elements and the spaces between them, as will be appreciated by those of ordinary skill in the relevant art. Although device 100 of the illustrated implementations is thus designed to hold a circular optical element, those of ordinary skill in the art will readily appreciate that the attributes described herein, including the circularity of the illustrated implementation, may readily be adjusted to accommodate a wide range of shapes and dimensions.

In particular implementations suitable for use with optical elements of a scanner, device 100 may have the following general specifications. Device 100 may be fabricated from a single piece of material such as a metal, plastic, metal alloy, alloy, or graphite composite. In some applications, metals or metal alloys are preferred materials, such as half-hard stainless steel, beryllium copper alloys, or aluminum; or full hard brass. More generally, device 100 may be made of one-piece stamped or photo-etched springy thin sheet metal. For example, in some applications device 100 may be made of semi-flexible thin metal or possibly plastic material, preferably at least 0.003, 0.004, 0.006, 0.008 or 0.010 inches thick, and possibly as much as 0.025 inches thick for low Young Modulus material. The material maybe no more than 0.1, 0.09, 0.08, or 0.07 inches thick for typical applications, and a thickness of approximately 0.006 inches thick may be preferred for some applications. Thickness, however, generally is dependent on the material used, and the above values are based on device 100 being made of 300, 400 or 700 series half-hard stainless steel. Device 100 may be manufactured by photo-etching, stamping, injection molding or in accordance with any of a variety of other conventional techniques. The selection of these techniques, or others that may be developed in the future, typically depend in part on the material chosen, as will be evident to those of ordinary skill in the relevant art.

The dimensions of various components of device 100 may vary widely depending on the dimensions of the part to be attached, its weight, the forces that are anticipated to possibly be applied to the part, the material used to fabricate device 100, and other factors. In one illustrative implementation, device 100 is made of half-hard stainless steel as specified above, having a thickness of approximately 0.006 inches. In this implementation, base 105 is a square having sides of 1.300 inches that, as shown in FIG. 1, may be rounded at the corners. Length 120 of illustrative holding member 112A (and the length of similar holding members 112B–D, all of which may hereafter be generally and collectively referred to as holding members 112) may be approximately 0.20 inches and its width approximately 0.13 inches. The distance between holding members, such as between member 112D and 118C, may be approximately 0.06 inches near their bases, although the separation regions may be rounded (e.g., half-circles of diameter 0.06 inches) where they abut base 105, as shown in FIG. 1. The lengths of holding members 114A–D and similarly shaped members 118A–D (generally and collectively, 114 and 118, respectively), as well as the lengths of holding members 116A–D (generally and collectively, 116), may be approximately 0.13 inches.

It will be understood that the number, shapes, and distributions of these holding members are illustrative only. As but one example, the illustrative dimensions given above for one or more parts of device 100 may be increased or decreased by ten-fold or more in any increment. As also noted, the shape of the attachment device may vary over a wide range so that it may encircle a part in the shape of an oval, square, rectangle, triangle, hexagon, or of any other shape, including irregular ones, and of a great variety of sizes and weights. Also, more or fewer holding members may be employed and otherwise distributed in other implementations.

Attributes of the holding members according to the present invention are now described in greater detail with respect to FIGS. 2A–C. FIGS. 2A–C are cross-sectional side views showing selected holding members of device 100 engaging an optical element 200A that may, for example, be illustratively assumed to be a mirror. In FIG. 2A, opposing holding members 112D and 112B are disposed to press against a top surface of mirror 200A so as to press it against support structure 250 and thereby hold mirror 200A and resist movement. In particular, members 112 are designed to have a length such that they extend beyond side surfaces 205A and 205B (that may be the same surface, as in the case of a circular lens or mirror) and thus at least partially engage top surface 207 of mirror 200A when mirror 200A is engaged with device 100. It is assumed for sake of illustration that mirror 200A is a circular mirror having a top surface 207, a bottom surface 208, and a thickness 210 between the top and bottom surfaces. Thus, members 112 are designed to have a length 120 such that the distance between opposing ones of members 112 is less than the diameter of mirror 200A. The length of members 112 further is determined by thickness 210 and thus the angle by which members 112 are flexed when mirror 200A is fully engaged with device 100 (i.e., in this example, bottom surface 208 of mirror 200A is on the same plane as the bottom of device 100). Members 112 center the mirror 200A as well as prevent lateral motion. As shown in FIG. 2A, it may often be acceptable for members 112 to be designed to overlap upper surface of the mirror 200A so as to press down on it and hold it. Geometrical considerations to be taken into account to achieve this consequent flexible engagement with top surfaces of elements of other shapes will now readily be appreciated by those of ordinary skill in the relevant art.

Because device 100 is made of a flexible material, the lifting of members 112 by engagement with mirror 200A typically causes flexing and/or twisting in portions of base 105 near the lifted members, thereby also partially lifting nearby holding members 114 and 118. For example, FIG. 2B shows illustrative, opposing holding members 118C and 118A (the cross section of FIG. 2B is taken through a different axis than that of FIG. 2A to more clearly show these holding members) lifted or flexed above base 105 of device 100. Advantageously, the length of members 114 and 118 are designed so that, in consideration of the diameter of circle 110, the nominal diameter of mirror 200A, and the thickness of mirror 200A, they will flexibly engage a side surface of mirror 200A. For example, illustrative members 118C and 118A are designed to be shorter than members 112 so that they engage side surfaces 205A and 205B, respectively. As will be appreciated by those of ordinary skill in the relevant art, if the nominal diameter of mirror 200A is greater than or less than its nominal diameter, holding members 114 and 118 will engage side surfaces of mirror 200A more or less nearer the top or nearer the bottom of mirror 200A. Members 114 and 118 of this example thus are disposed to provide pressing and resisting functions for optical elements of a range of diameters around a nominal value and thus provide tolerance for deviations from nominal. An additional advantage of providing members such as 114 and 118 that engage a side surface above a bottom surface of the optical element is that optical elements often are built with beveled edges to guard against chipping, and thus engagement along a mid portion of a side surface, as opposed to just along the top or bottom of a side surface, typically is desirable.

As noted, the lifting of members 112, in addition to causing lifting of members 114 and 118 of this example, also typically causes lifting of adjacent portions of base 105. However, other portions of base 105 are not lifted because they are secured to support structure 250 (as shown in FIG. 2C). Thus, base 105 twists and/or flexes, as indicated in FIGS. 2A–C in which FIG. 2A shows the lifting of a portion of base 105 near member 112B above structure 250 by a small distance 201, FIG. 2B shows the lifting of a portion of base 105 near member 118A above structure 250 by a small distance 202, and FIG. 2C shows portions of base 105 near securing element 260 firmly attached to structure 250.

FIG. 2C shows substantially rigid engagement by holding members 116 with mirror 200A. This substantial rigidity is achieved because members 116 lie substantially flat in the plane of the top surface of device 100, or raised slightly above it. They function to hold mirror 200A against high accelerations possibly caused by shock to the instrument such as may be experienced if the instrument is dropped. In particular, radial forces in substantially the plane of device 100, such as illustrative force 280, are resisted by members 116 due to their lack of compression and the fixed relationship of members 116 to support structure 250 as provided by securing elements 260. Members 116 remain substantially flat when device 100 is engaged with mirror 200A because members 116 are relatively far from highly flexed members 112, and are far enough from moderately flexed members 114 and 118, so that base 105 in the vicinity of members 116 does not flex so as to cause members 116 to rise. As will now be appreciated by those of ordinary skill in the relevant arts in view of this disclosure, the desired lack of flexing of base 105 and of members 116 depends on factors such as the flexing (e.g., bending or twisting) characteristics of the material of which device 100 is fabricated, the geometry of mirror 200A, the shape of the holding elements and spaces between them, the distances between the holding elements, the placement of securing elements 260, and so on. The substantial rigidity of holding members 116 provides protection against radial movement of mirror 200A that, as illustratively noted above, typically is an important objective in the deployment of lenses, mirrors, and other optical elements.

FIG. 3 is a cross-sectional side view of device 100 engaging another optical element that is illustratively assumed to be a lens 200B. FIG. 3 shows an implementation of device 100 designed to retain optical elements that are comparatively thick as compared with their diameter, such as is typical of high performance mirrors or lenses with highly curved surfaces. It should be noted that in this case, base 105 is dimensioned to permit sufficient twist for holding members 112 to reach high over support structure 250.

Opposing holding members 112 flexibly engage, at least partially, a top surface of lens 200B and thus hold lens 200B, through base 105, to support structure 250 in a manner similar to the operation of members 112 with respect to engagement with mirror 200A of FIG. 2A. Opposing holding members 114B and 118C engage a side surface of lens 200B, thus providing tolerance for varying diameters of lens 200B while providing resistance to movement and holding, as was shown in the previous example of FIG. 2B. Opposing holding members 116B and 116C provide relatively rigid engagement with lens 200B so as to prevent radial movement, as noted above with regard to the example of FIG. 2C. It may illustratively be assumed that base 105 is welded to support structure 250 in this example.

Figure 4:
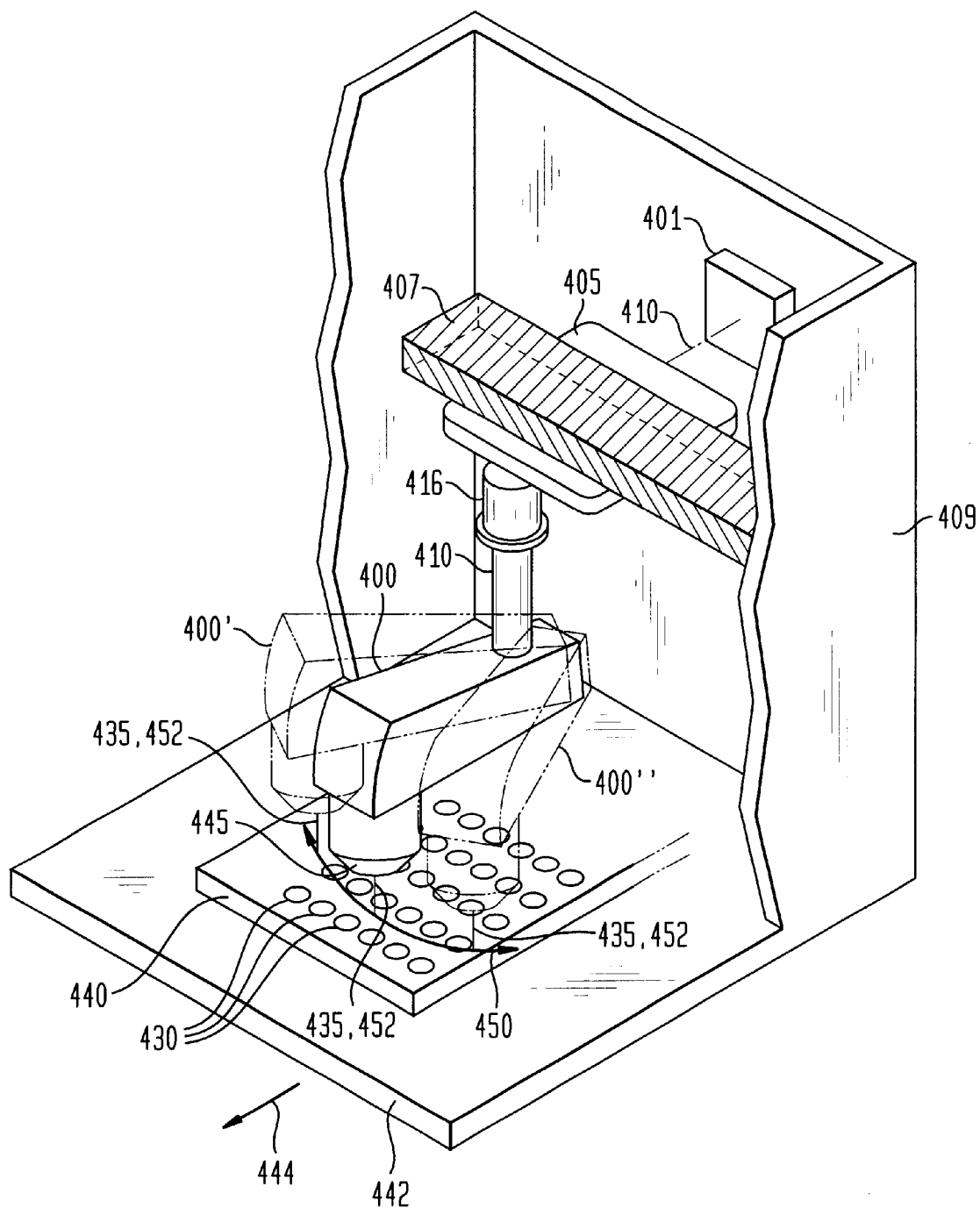
FIG. 4 is a simplified perspective cutaway view of one embodiment of a scanner employing an illustrative attachment device such as shown in FIG. 1.

FIG. 4 is a partial perspective cutaway view of a simplified scanner 409 suitable for scanning probe features 430 on a substrate 440 of a probe array. For example, scanner 409 may be a scanner such as described in U.S. Provisional Patent Application No. 60/286,578, incorporated by reference above. Scanner 409 includes an illustrative attachment device 405 similar to device 100. Attachment device 405 holds a mirror (obscured in this view) and is itself secured to structural element 407. An oscillating arm 400 scans along an arc 450 as a translation stage 442 moves in a direction 444 under the arm. Arm 400 is shown in alternative positions 400' and 400" along its arcuate path. Laser light from laser source 401 follows path 410 to strike the mirror hidden from this view under attachment device 405, thereby being deflected down a vertical optical axis of periscope 416, thence again deflected by first and second mirrors (not shown) in arm 400 to emerge through objective lens 445 as excitation beam 435. Beam 435 excites fluorophores attached to target molecules that have hybridized with certain of probes 430. Fluorescent emission beam 452 returns through arm 400 via path 410, including being reflected from the mirror held by device 405. It will be understood that, for clarity, other optical elements are not shown that direct the emission beam to a detection device, such as a photomultiplier tube (also not shown).

Having described various embodiments and implementations, it should be apparent to those skilled in the relevant art that the foregoing is illustrative only and not limiting, having been presented by way of example only. Other schemes for distributing functions among the various functional elements of the illustrated embodiment are possible. For example, the flexing and flexible engaging ascribed herein to a holding element may be carried out, in whole or in part, by a support region associated with the holding element. The functions of any element may be carried out in various ways in alternative embodiments. Also, the functions of several elements may, in alternative embodiments, be carried out by fewer, or a single, element. Numerous other embodiments, and modifications thereof, are contemplated as falling within the scope of the present invention as defined by appended claims and equivalents thereto.

What is claimed is:

1. A device for attaching a part to a structure, comprising:
    a base;
    a first plurality of holding elements coupled to the base including a first holding element of a first length and a second holding element of a second length shorter than the first length, wherein each holding element is adapted and constructed to flexibly engage at least one surface of the part; and a second plurality of holding elements including a plurality of opposing holding elements constructed and arranged to rigidly engage opposing side surfaces of the part wherein the base and the plurality of opposing holding elements are constructed and arranged to form a substantially flat surface when the device is not engaged with the part.

2. The device of claim 1, wherein:

the device is formed from a single piece of flexible material.

3. The device of claim 1, wherein:

two or more opposing holding elements of the first plurality of holding elements exert forces on at least one surface of the part due, at least in part, to deformation of the opposing holding elements from the substantially flat surface when the device is engaged with the part.

4. The device of claim 3, wherein:

the forces exerted by the opposing holding elements are due, at least in part, to deformation of a portion of the base from the substantially flat surface when the device is engaged with the part.

5. The device of claim 3, wherein:

each of the forces includes a component perpendicular to the substantially flat surface.

6. The device of claim 3, wherein:

each of the forces includes a component parallel to the substantially flat surface.

7. The device of claim 3, wherein:

the first and second holding elements are adjacent to each other; and when the device is engaged with the part, the second holding element is deformed from the substantially flat surface due, at least in part, to the first holding element being deformed from the substantially flat surface.

8. A device for attaching an optical element to a structure, comprising:

a base;

a first plurality of holding elements coupled to the base including a first holding element of a first length and a second holding element of a second length shorter than the first length, wherein the first holding element is constructed and arranged to flexibly engage a top surface of the optical element and the second holding element is constructed and arranged to flexibly engage a first side surface of the optical element when the device is engaged with the optical element; and a second plurality of holding elements including a plurality of opposing holding elements constructed and arranged to rigidly engage opposing second and third side surfaces of the part;

wherein the base and holding elements are formed of a single piece of flexible material having a substantially flat surface, and wherein two or more holding elements of the first plurality of holding elements exert forces on at least one surface of the optical element due, at least in part, to their deformation from the substantially flat surface when the device is engaged with the optical element.

9. The device of claim 8, wherein:

the first side surface is a same surface as either the second side surface or the third side surface.

10. A scanner, comprising:

an optical element;

a support structure; and a device constructed and arranged to attach the optical element to the support structure, comprising (a) a base having at least one securing element adapted and constructed to secure the device to the support structure, (b) a first plurality of holding elements coupled to the base including a first holding element of a first length and a second holding element of a second length shorter than the first length, wherein the first holding element is constructed and arranged to flexibly engage a top surface of the optical element and the second holding element is constructed and arranged to flexibly engage a first side surface of the optical element, and (c) a second plurality of holding elements including a plurality of opposing holding elements constructed and arranged to rigidly engage opposing second and third side surfaces of the optical element;

wherein the base and first and second pluralities of holding elements are formed of a single piece of flexible material having a substantially flat surface, and wherein two or more opposing holding elements of the first plurality of holding elements exert forces on at least one surface of the optical element due, at least in part, to their deformation from the substantially flat surface when the device is engaged with the optical element.

11. A device for holding an optical element in a semi-rigid manner, comprising:

a base;

a first plurality of deformable elements of a first length; and a second plurality of deformable elements of a second length shorter than the first length, wherein the deformable elements are coupled to the base so as to wholly or partially surround the optical element and retain it by applying axial and lateral forces; wherein the base and deformable elements are formed from a single piece of material.

12. The device of claim 11, wherein:

the base includes at least one twisting region that cooperates with at least one deformable element to hold the optical element in a semi-rigid manner.

13. The device of claim 11, wherein:

the base includes at least one bending region that cooperates with at least one deformable element to hold the optical element in a semi-rigid manner.

14. A scanner, comprising:

a support structure;

an optical element; and a device for attaching the optical element to the support structure in a semi-rigid manner, comprising a b se; a first plurality of deformable elements of a first length; and a second plurality of deformable elements of a second length shorter than the first length; wherein the deformable elements are coupled to the base so as to wholly or partially surround the optical element and retain it by applying axial and lateral forces, wherein the base and deformable elements are formed from a single piece of material.

* * * * *